United States Patent [19]
Lewis

[11] Patent Number: 5,052,215
[45] Date of Patent: Oct. 1, 1991

[54] LEAK DETECTION IN STORAGE TANK BOTTOMS BY PNEUMATIC ENHANCEMENT OF ACOUSTIC EMISSIONS

[76] Inventor: Donald E. Lewis, 7714 Moritz Lake Dr., Corpus Christi, Tex. 78413

[21] Appl. No.: 599,890

[22] Filed: Oct. 18, 1990

[51] Int. Cl.⁵ .............................................. G01M 3/24
[52] U.S. Cl. ................................... 73/40.5 A; 73/49.2
[58] Field of Search .................. 73/40.5 A, 49.2, 40.7, 73/592

[56] References Cited

U.S. PATENT DOCUMENTS

| | | | |
|---|---|---|---|
| 2,460,054 | 1/1949 | Wiggins | 73/49.2 X |
| 4,176,543 | 12/1979 | Nolte et al. | 73/40.5 A |
| 4,413,503 | 11/1983 | Olivieri | 73/49.2 X |
| 4,462,249 | 7/1984 | Adams | 73/49.2 X |

*Primary Examiner*—Hezron E. Williams
*Attorney, Agent, or Firm*—Head & Johnson

[57] ABSTRACT

A system and method for injecting gas or fluid in the base beneath an above ground storage tank to enhance the rate of any leakage in the bottom of the tank, and detecting and locating the leak by acoustic sensors placed about the tank. The leak may then be sealed by injecting sealant through a probe placed beneath the tank in the area of the leak.

9 Claims, 3 Drawing Sheets

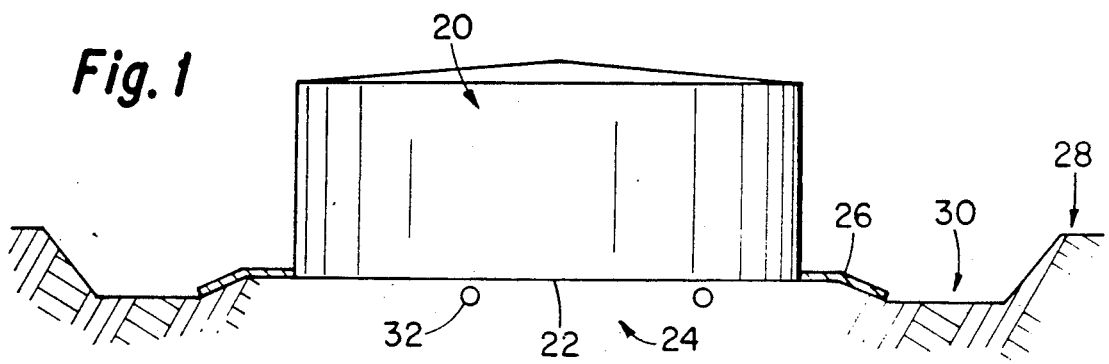
Fig. 1
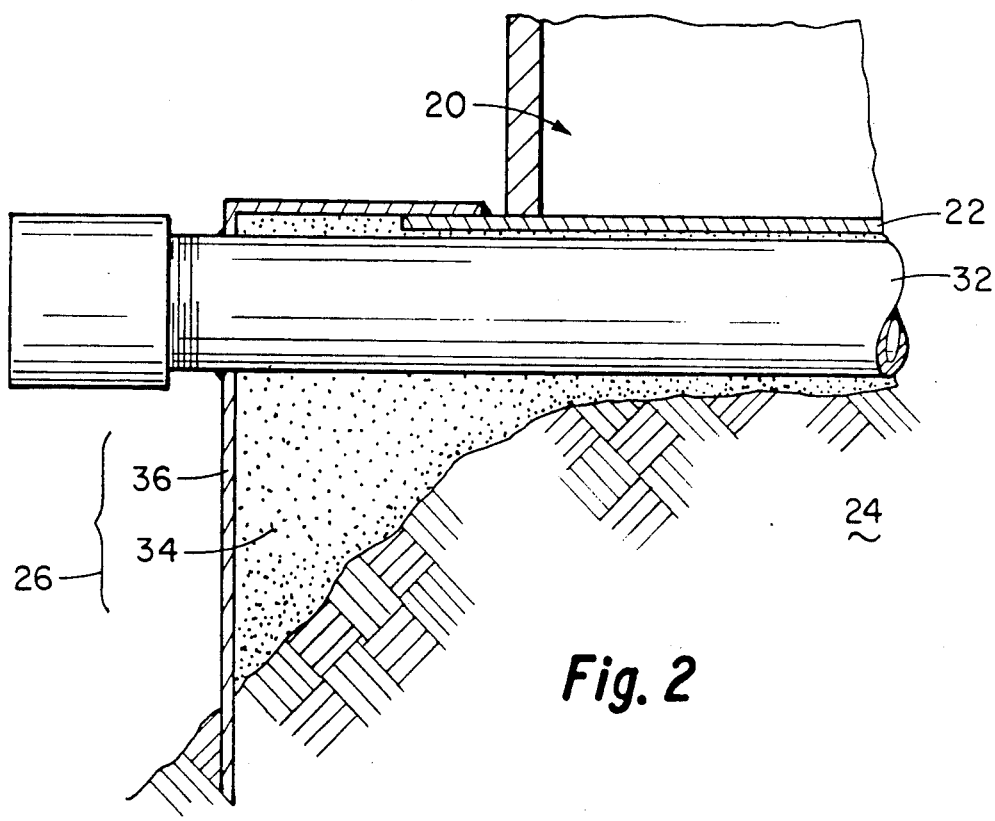
Fig. 2
Fig. 3

LEAK DETECTION IN STORAGE TANK BOTTOMS BY PNEUMATIC ENHANCEMENT OF ACOUSTIC EMISSIONS

CROSS-REFERENCES

This application is an improvement of my prior patent: Lewis, U.S. Pat. No. 4,896,528, Jan. 30, 1990; the disclosure in this cited prior patent is hereby incorporated by specific reference into this application.

DISCLOSURE STATEMENT

Related art includes the articles:

1. *Nondestructive Examination of Above Ground Storage Tanks for Leak Detection*, by Allen T. Green (Hartford Steam Boiler Inspection Technologies, Sacramento, Cal.), and Robert W. Lauben (The Hartford Steam Boiler Inspection and Insurance Co., Hartford, Conn.).
2. *Acoustic Emission Monitoring of Above-Ground Storage Tanks*, by C. M. Nickolaus, *Materials Evaluation*, 46/Mar. 1988.
3. *Acoustic Emission Source Location in Two Dimensions by an Array of Three Sensors*, by A. Tobias, *Nondestructive Testing*. Vol. 9, No. 1, Feb. 1976, pages 9–12.

Attention is also directed to the art cited in U.S. Pat. No. 4,896,528, a related patent, and to the following U.S. Pat. No(s):

| | | | |
|---|---|---|---|
| 1. | 3,442,349 | 05/06/1969 | Bosselaar |
| 2. | 3,478,576 | 11/18/1969 | Bogle |
| 3. | 3,838,593 | 10/01/1974 | Thompson |
| 4. | 4,327,576 | 05/04/1982 | Dickey et al |
| 5. | 4,858,462 | 08/22/1989 | Coulter et al |
| 6. | 4,899,573 | 02/13/1990 | Dimmick et al |
| 7. | 4,901,576 | 02/20/1990 | Rademacher |

'349 is an Acoustic Pipeline Leak Detector which travels through a pipeline and carries an acoustic detector, such as a piezoelectric apparatus for detecting leaks, and an attached recorder, all mounted on a wheel.

'576 is an Acoustic Leak Detecting Apparatus and Method which is a device for detecting leaks within a pipeline using two detectors mounted on a "pig" so that the signals received are paired so as to delete background noise.

'593 is an Acoustic Leak Location and Detection System used mainly for detecting leaks in storage tanks with moveable sensors whose output is amplified, compared and analyzed to locate the leak.

'576 is an Acoustic Leak Detector used for detecting leaks in a pipeline using a two channel electronic/transducer configuration with amplification and averaging of the wavelength signals to locate the leak.

'462 is an Acoustic Emission Leak Source Location using spaced detectors and comparison of signals therefrom to locate leaks.

'573 is an Apparatus and an Associated Method for Leak and Volume Inspection of containers which tests commercial containers for leaks and for volume accuracy by comparing an unknown container with a control container using bursts of pressure and acoustical detection of leaks.

'576 is an Acoustic Leak-Detection System used primarily for detecting leaks or defects in car bodies by projecting high frequency sound toward one side of the body and detecting leaks by microphones.

BACKGROUND OF THE INVENTION

Field of the Invention

This invention relates to the field of leak detection by acoustical means in storage tanks.

Description of the Related Art

One of the most common ways of storing hydrocarbons, such as crude oil, gasoline and the like is in large metal storage tanks which are normally cylindrical in shape with the bottom resting on a base of soil or other material. Many precautions are made to improve the engineering of these tanks to prevent them from leaking. However, despite all of this effort these tank do develop leaks. These leaks are harmful in at least two ways: (1) They can cause pollution of the underground soil and possibly underground water sources; and (2) the loss of the material itself is loss of a natural resource and this can also be costly in terms of dollars. For example, if one tank leaks more that two barrels of fluid per day the loss would be more than 30,000 gallons per year. These tanks may be 100 to 200 feet in diameter and may contain upward to 100,000 or more barrels of fluid. If there are 25 such tanks in a tank farm then there could be a leakage of as much as 750,000 to 2,000,000 gallons of fluid per year.

Acoustical detection of leaks in the bottom of storage tanks usually consists of placing multiple sensors around and in the tank and connecting such sensors to amplifying, analyzing and display means. Since the passage of fluid through a leak creates vibrations, this is an "acoustical event" that may be detected and localized.

Acoustical leak detectors usually require that a leak be "active" to be detectable (i.e. the leak must be passing material to create turbulence which is acoustically detected). Leaks which are equilibrated with no passage of materials are not detectable by present acoustical methods; likewise leaks with a very low flow rate are difficult to detect. Prior attempts to overcome these limitations have included: (1) varying the liquid storage levels in tanks to force fluid out of the leaks to generate a detectable sound; (2) requiring absolute silence in and around the tank; (3) using prolonged testing times, often over an hour. Generally, small leaks (less than ⅛th inch) are not detectable by prior art means.

SUMMARY OF THE INVENTION

It is an object of this invention to provide a method and apparatus to detect leaks in the bottom of large fluid storage tanks and to determine the location of such leaks in order to repair them.

It is a further object of this invention to provide a means of using positive pressure to enhance the flow rate (pneumatic enhancement) through a leak thus facilitating the detection of such leak.

In the preferred embodiment, one or more perforated conduits are inserted beneath the storage tank in the base below the bottom of the tank. The perforations may be in the end and/or side of the conduit. Gas, or other suitable fluid, is injected under positive pressure into the conduit with sufficient pressure to force the gas out of the perforations in the conduit into the base thus forming a plenum of positive pressure beneath the bottom of the tank. This pressure pushes upward on the tank bottom, and causes material to move through any leaks that may be in the bottom of the tank. In order to facilitate the retention of the pressure beneath the tank, it may be necessary to place a seal around the periphery of the base.

A plurality of acoustical sensors are placed around and/or within the tank and detect any acoustical event generated by movement of material through leaks in the bottom of the tank. These sensors may be microphones, piezoelectric, or other suitable types.

The signals generated by the various acoustical sensors are amplified and analyzed. Analysis may be by triangulation methods or by signal comparison methods as in Coulter, U.S. Pat. No. 4,858,462. This allows the location of the leak to be identified. Once the site of leakage is known, then a perforated probe may be inserted under the tank and a settable sealant may be injected into the base through the probe in the area abutting against the tank bottom at the point of the leak to form a seal, much as disclosed in my prior U.S. Pat. No. 4,896,528.

BRIEF DESCRIPTION OF THE DRAWINGS

FIG. 1: Sideview of a storage tank.

FIG. 2: Closeup, cutaway sideview of the seal around the periphery of the base.

FIG. 3: Partially cutaway sideview of a segment of conduit.

DESCRIPTION OF THE PREFERRED EMBODIMENT

Figure 6:
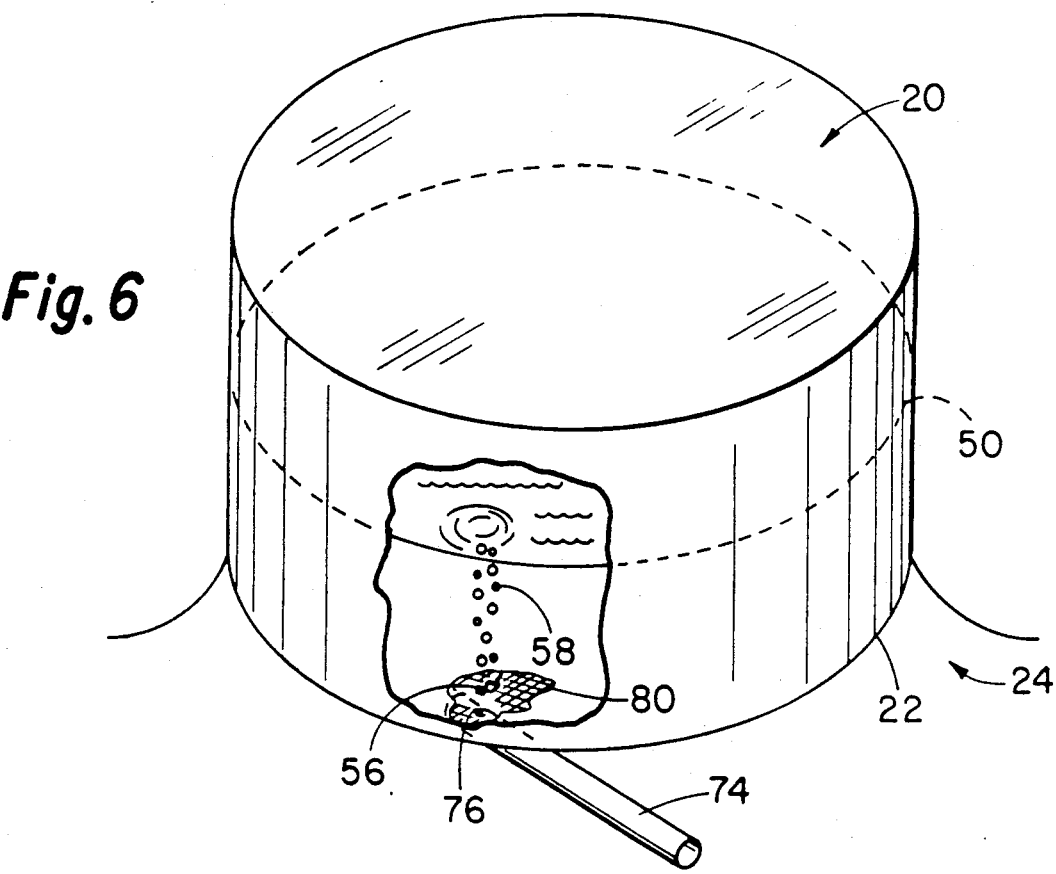
FIG. 6: Isometric, partially cutaway view of storage tank showing probe with sealant being injected under tank.

FIG. 1 illustrates a storage tank 20 with the bottom of the tank 22 resting on a base 24 with a seal 26 around the periphery of the base 24. A dike 28 and moat 30 surround the tank 20 to retain any spills that may occur. Within the base 24 one or more perforated conduits 32 are in place.

The base 24 can be formed of any suitable material, such as soil, sand, gravel, crushed rock and the like. The seal 26 may not be necessary in all cases. If the base 24 is very porous, then a seal 26 probably will be necessary. The seal 26 may be plastic, metal, or other nonporous materials. FIG. 2 illustrates one embodiment of a seal 26 in which the base 24 has a layer of grout 34 around the periphery, and a sealing skirt 36 over the group 34. The perforated conduit 32 passes through the skirt 36 and grout 34 into the base 24 below the bottom of the tank 22.

Turning now to FIG. 3, a segment of perforated conduit 32 is shown in cut-away detail. The conduit 32 has a wall 38, a lumen 40 and one or more perforations 42. The conduit 32 may be formed of metal, plastic or other suitable material. The perforation(s) 42 may be in the side, as illustrated, or in the tip (not illustrated), or both. In use, gas or fluid is injected under pressure into the conduit 32, illustrated by arrow 44, and through the lumen 40 of the conduit, and out the perforation(s) 42 into the base. This flow is illustrated by arrow 42. In the preferred embodiment, gas is injected with sufficient pressure to force flow through the perforation(s) 42. Any suitable commercially available gas or fluid may be used.

The injected gas or fluid noted above, passes into the base 24 beneath the tank 20. If there is a leak in the bottom of the tank 22, the increased pressure beneath the tank will either cause the injected gas or fluid to pass through the leak, or it will disturb any equilibrium that may be stopping or decreasing flow through the leak, so that there is increased flow through the leak. This flow through the leak creates vibrations, i.e. an acoustically detectable event, which may be detected by acoustic sensors.

Figure 4:
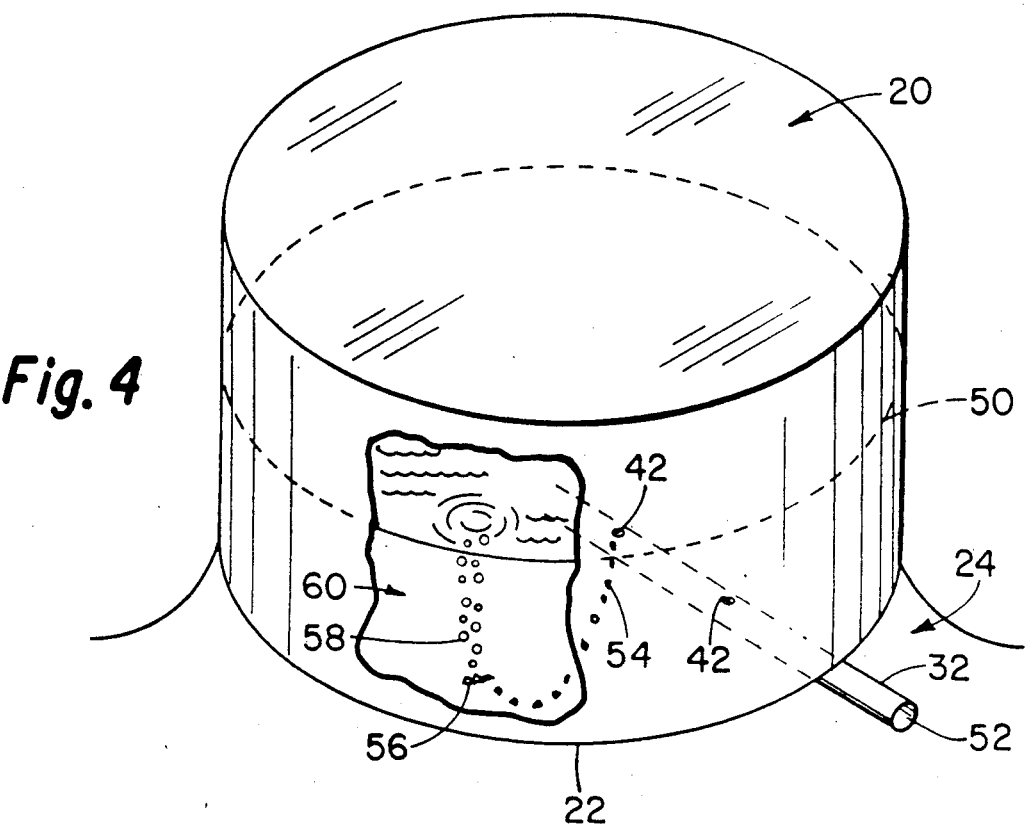
FIG. 4: Isometric, partially cutaway view of storage tank showing conduit in place and gas flow under tank and and through leak.

FIG. 4 illustrates the above sequence. A perforated conduit 32 is inserted into the base 24 beneath the tank 20. The conduit 32 is generally horizontally placed in a parallel relation to the bottom of the tank 22. The tank 20 has liquid in it with at a certain level 50. Gas or fluid is injected under pressure into the conduit end 52, this flows through the conduit 32 and out the perforations 42 in the conduit into the base 24 area. In FIG. 4 a line of bubbles 54 is shown flowing from the perforation 42 in the conduit 32 through the base 24 to a leak 56 in the bottom of the tank. The gas is then shown flowing through the leak 56 as another series of bubbles 58 within the liquid 60 in the tank.

Figure 5:
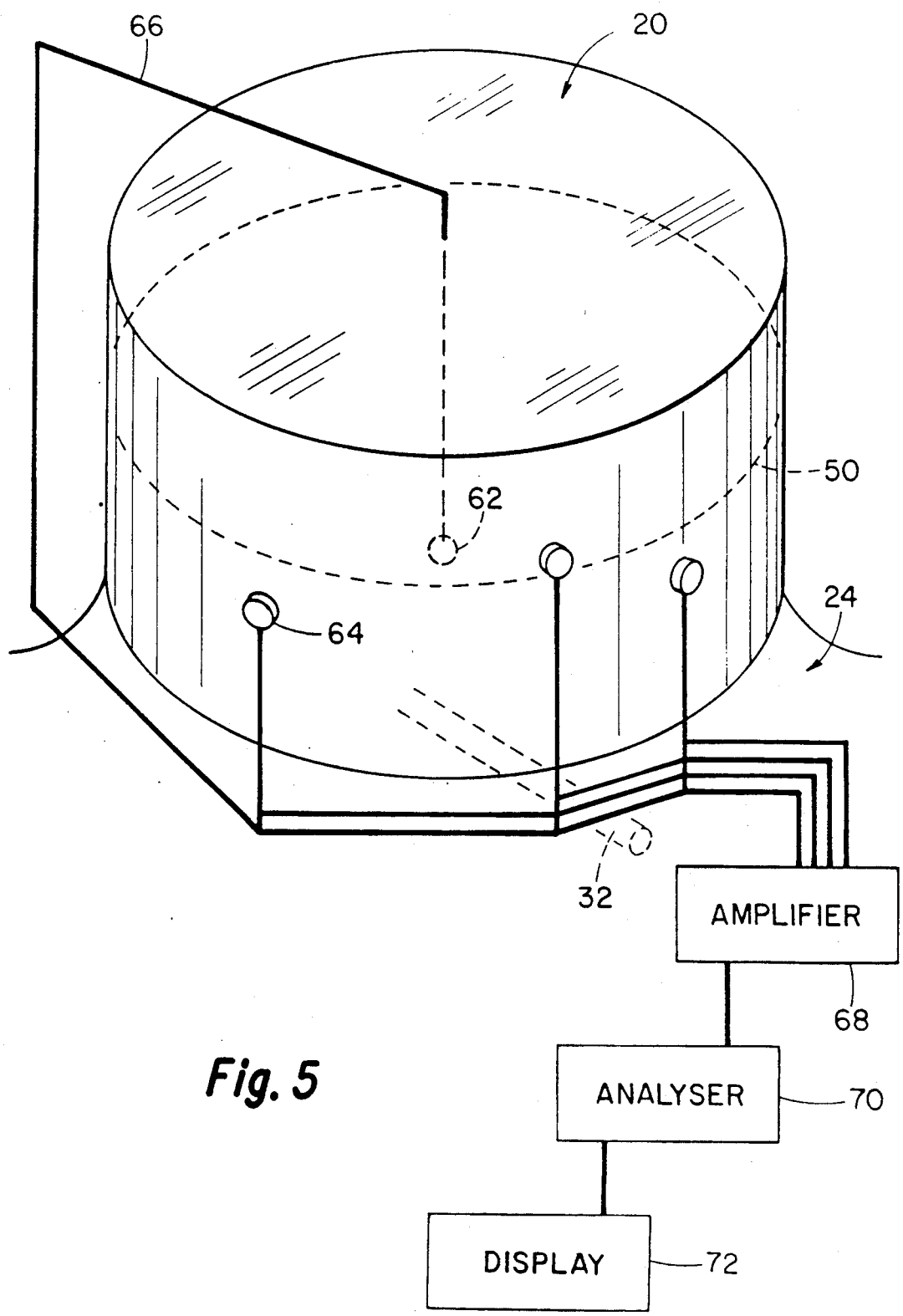
FIG. 5: Isometric view of storage tank with attached sensors, and block diagram.

Attention is now directed to FIG. 5. This illustrates the tank 20, on a base 24, with a conduit 32 beneath the tank. Acoustic sensors are also shown. These may be internal sensors 62 within or below the liquid level 50 inside the tank; or, they may be external sensors 64 placed outside the tank 20. Various combinations and numbers of sensors may be used. Sensors may be of any available type, such as piezoelectric, microphones, and the like. The sensors 64 and 62 are attached by cables or wires 66 to an amplifier 68, an analyzer 70, and a display 72. If my invention is only used to screen for leaks, then only 1 or 2 sensors may be needed, and no analysis or display is needed, since one is only screening to see if there is a leak. However, if one wishes to locate the site of the leak, a plurality of sensors will be needed with amplification and analysis of the signals from the sensors and display of the results.

Once a leak is detected and located, the user may wish to seal the leak. While the tank can be drained, and conventional repair methods used, this invention offers an alternative. This is illustrated by FIG. 6. Once the leak 56 is located, a probe 74 is inserted beneath the tank 20 in the base 24 in a horizontal position. The probe 74 has a perforation 76 either in the side or tip of the probe. The probe 74 is positioned in the base 24 so that the perforation 76 lies below and near the leak 56. A settable sealant is then injected under pressure through the probe 74 so that it is extruded from the perforation 76 and will flow into the area abutting the leak 56 and will seal the leak. This exuded sealant is indicated in FIG. 6 at 80.

I have tested the above described pneumatic enhancement of acoustic emissions and found:

(1) I have been able to detect leaks as small as 0.02 inches.

(2) I have been able to detect leaks within 2 minutes of the start of the test. This is compared to several hours required in some other methods. Further, this reduces the time of exposure to background noise.

(3) I was able to detect leaks in spite of background noise. For example, in one case there was a sand blasting operation about 100 yards away with the air compressor 15 feet from the test tank, and I was still able to detect leaks.

I did these tests in a tank with 18 inches of liquid contents. The plenum pressure under the tank can be varied in response to the acoustic output as needed.

As noted in my prior U.S. Pat. No. 4,896,528, one way of placing the perforated conduit and/or probe beneath the tank is to use the "HOLE-HOG" (reg. trademark) available from Cimmac, Inc., 4251 South 76th East Avenue, Tulsa, Okla. 74147 which is used for drilling horizontal holes.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

I claim:

1. A system for detecting leaks in the bottom of a storage tank which sits on a base, comprising:
   at least one perforated conduit inserted in said base beneath said tank;
   means of injecting gas under positive pressure into said conduit; and
   at least one acoustical sensor placed about said tank in a position so that the sensor can detect any acoustic event created by passage of said gas through said leaks in said tank bottom.

2. The system as defined in claim 1 which further comprises:
   means for amplifying any signals detected by said acoustical sensors;
   means for analyzing said amplified signals; and
   means for displaying said analysis results such as to show the area of leakage.

3. The system as defined in claim 1 in which at least one acoustic sensor is suspended within the tank, and at least one acoustic sensor is in direct contact with the wall of said tank.

4. The system as defined in claim 1 in which at least three acoustic sensors are spaced apart on the wall of said tank.

5. The system as defined in claim 2 further comprising:
   a probe inserted in the base beneath said tank in the area of leakage through which sealant may be injected to plug said leak.

6. A system for detecting leaks in the bottom of a storage tank which sits on a base, comprising:
   at least one perforated conduit inserted in the base beneath said tank;
   means of injecting fluid under pressure into said conduit; means of sealing the periphery of said base to retain pressure therein;
   a plurality of acoustic sensors mounted about said tank capable of detecting any acoustical events created by said fluid under pressure passing through a leak in the bottom of said tank;
   means of amplifying signals derived from said acoustic sensors;
   means of analyzing and displaying said signals; and
   a probe placed within said base to inject sealant in the area of leakage.

7. A method for pneumatically enhancing the acoustical emissions from leaks in the bottom of a storage tank which sits on a base, and for detecting said emissions, comprising:
   installing at least one perforated test conduit in said base beneath said storage tank;
   injecting fluid under positive pressure into said conduit;
   placing a plurality of acoustic sensors about said tank so as to detect any acoustic signal generated by the passing of material through said leak in the bottom of said tank; and
   amplifying, analyzing and displaying any output of said sensors.

8. The method of claim 7 further comprising the step of sealing the periphery of the base to prevent escape of injected fluid.

9. The method of claim 7 further comprising the steps of:
   inserting a perforated probe beneath said tank in the area of said leak; and
   forcing a settable sealant through said probe such that the sealant exits the perforation in said probe and forms a seal over the leak in said tank bottom.

* * * * *